United States Patent [19]

Ferguson

[11] Patent Number: 5,575,237
[45] Date of Patent: Nov. 19, 1996

[54] METHOD OF HATCHING AVIAN EGGS

[75] Inventor: Mark W. J. Ferguson, Stockport, England

[73] Assignee: The Victoria University of Manchester, England

[21] Appl. No.: 481,428

[22] PCT Filed: Dec. 16, 1993

[86] PCT No.: PCT/GB93/02565

§ 371 Date: Aug. 23, 1995

§ 102(e) Date: Aug. 23, 1995

[87] PCT Pub. No.: WO94/13132

PCT Pub. Date: Jun. 23, 1994

[30] Foreign Application Priority Data

Dec. 16, 1992 [GB] United Kingdom ............ 9226179

[51] Int. Cl.$^6$ .................................................. A01K 41/00
[52] U.S. Cl. ............................ 119/68; 119/300; 119/311
[58] Field of Search ............................. 119/6.8, 174, 35, 119/300, 311

[56] References Cited

U.S. PATENT DOCUMENTS

| | | | |
|---|---|---|---|
| 2,704,531 | 3/1955 | Bailey | 119/35 |
| 2,734,482 | 2/1956 | Seltzer | 119/6.8 |
| 3,038,443 | 6/1962 | Miller | 119/35 |
| 3,147,737 | 9/1964 | Theilig | 119/35 |
| 5,090,617 | 2/1992 | Swan et al. | 263/3 |

FOREIGN PATENT DOCUMENTS

| | | |
|---|---|---|
| 0433084 | 6/1991 | European Pat. Off. . |
| 0514056 | 11/1992 | European Pat. Off. . |

*Primary Examiner*—Robert P. Swiatek
*Assistant Examiner*—Yvonne R. Abbott
*Attorney, Agent, or Firm*—Renner, Otto, Boisselle & Sklar, P.L.L.

[57] ABSTRACT

A method of hatching eggs of avian species, especially chickens, which comprises carrying out at least one cycle of steps (a) and (c) as follows: (a) incubating the eggs in a first, baseline ambient environment which is normal for hatchery incubation of the eggs of the avian species in the prevailing climatic conditions and then during a sex-sensitive time window of embryonic development, (b) altering the ambient environment to shifted conditions for a period of time effective to bias the normal phenotypic sex ratio of the embryos, without significant adverse effect on the average mortality rate, and (c) thereafter restoring the incubation conditions to or towards normal and allowing the eggs to hatch. Preferably the ambient environment comprises a temperature of 37.5°–38° C. and the shifted conditions comprise reduced temperature, especially a temperature maintained at about 22° C. for a period of from 18 to 42 hours. The method may be used to produce birds which are chromosomally male (ZZ) but phenotypically female or chromosomally female (ZW) but phenotypically male.

13 Claims, No Drawings

METHOD OF HATCHING AVIAN EGGS

BACKGROUND OF THE INVENTION

1. Field of the Invention

This invention relates to the hatching of eggs of avian species, especially of poultry birds, and to the hatchlings thus obtained, adult birds grown from the hatchlings and subsequent generations of birds bred from said adult birds.

2. Description of Related Art

Sex determination in avian species, including domestic poultry (chickens, turkeys, pheasants etc) is determined by genetic mechanisms. Female birds are heterogametic, with ZW chromosomes, whereas males are homogametic, with ZZ chromosomes (this is the reverse of the situation in mammals, where males (XY) are the heterogametic sex and females (XX) are the homogametic sex. It is assumed that there are genes on either the Z or the W chromosome, responsible for sex determination in birds. However, it is unclear whether the genes which regulate male or female development are present on the Z chromosome, the W chromosome or on some combination of these (e.g. an activator on the Z chromosome and an inhibitor on the W chromosome). What is clear however, is that in birds, as in mammals, sex is apparently determined at the time of fertilisation (Sittman 1984, and references therein).

By contrast, in some reptiles, the temperature of egg incubation determines the sex of the offspring; there being no heteromorphic sex chromosomes in either males or females (see Deeming and Ferguson 1988 for a review), It has therefore been supposed that there are two fundamental types of sexual determination in vertebrates: genetic (or chromosomal) sex determination as in birds and mammals, whereby the sex of the offspring is determined at the time of fertilisation and environmental (or temperature) determination in reptiles where sex is determined after fertilisation, as a result of interaction with some environmental agent.

There have been few previous investigations of the effects of temperature on sex ratio in birds, probably because deviations from the normal temperature in birds are usually lethal to the embryo (Bennett and Dawson 1979, Tazawa and Rahn 1986). In the domestic chicken, deviations from the preferred incubation temperature of 37.5° to 38° C. during incubation causes significant embryonic mortality. This situation in birds if very different from that In reptiles whose embryos are tolerant to a fairly wide range (often 5° C. or more) of incubation temperatures without any significant effect on embryonic mortality.

However, Shubina et al. (1972) have reported that a change in incubation temperature of chicken eggs can alter the sex ratio between male and female embryos. The paper begins by referring to an earlier paper which is said to have shown that a brief increase in incubation temperature in the period preceding or concurrent with gonadal differentiation of chicken embryos leads to the formation of primarily female individuals. There follows a description of experiments apparently showing that reducing the temperature of incubation after 72 hours from 37.5° C. to 22° C. for 7 or 8 hours biases the sex ratio towards males, namely to a 1.5:1 or 1.43:1, respectively, ratio of males to females. These figures are not encouraging because mortality of the embryos was 9.1 and 10.5% respectively, compared with 6.1% in the control group: see Table 1. However, all figures in Table 1 must be treated with caution, since it is unclear how to reconcile the percentage mortalities with the total number of embryos examined and the total number of eggs used. Also, one set of experiments seems to have been omitted from the results shown in Table 1. Thirdly, the paper reports in Table 2 a previous experiment in which the incubation temperature is increased to 41° C., yet the mortalities reported are only 7–12% and the bias is in favour of males.

SUMMARY OF THE INVENTION

The present invention provides a method of hatching eggs of avian species, especially of chickens, which comprises carrying out at least one cycle of steps (a) to (c) as follows:

a) incubating the eggs in a first, baseline ambient environment which is normal for hatchery incubation of the eggs of the avian species in the prevailing climatic conditions and then during a sex-sensitive time window of embryonic development, (b) altering the ambient environment to shifted conditions for a period of time effective to bias the normal phenotypic sex ratio of the embryos, without significant adverse effect on the average mortality rate, and (c) thereafter restoring the incubation conditions to or towards normal, and allowing the eggs to hatch.

The eggs will normally be incubated at 37.5° C.–38° C. The alteration of the ambient environment to shifted conditions normally takes the form of a reduction in temperature of incubation, especially to either about 22° C. or to about 36° C., whereby the sex ratio of hatchlings is biased in favour of males or females respectively.

The terminology "without significant adverse effect on mortality rate" implies that it is readily possible to find conditions in which the mortality is below 9% as determined on embryos at day 10 of incubation. More preferably, mortality is below that of control eggs incubated at a constant 38° C. These conditions differ from those of Shubina et al. supra, especially in respect of the period of time during which the temperature is shifted, also referred to herein as "pulse time".

To carry out the method an incubator should be adapted to carry out a cycle of steps (a) to (c) preferably by the provision of associated programmable control means for varying the ambient conditions referred to, especially temperature. point data, places in the incubator where eggs could be placed to ensure uniform incubation temperature were determined. In all subsequent experiments, eggs were placed in these uniform temperature zones within the incubator. Further, it was observed that when the incubator lid was opened for more than 5 minutes, then the temperature in the incubator rose to above that at which it was set. This was obviously a function of the thermostat, activating the heater in the incubator to warm it up again. It was determined in early experiments that these temperature spikes were detrimental to the eggs and complicated the experiments. Accordingly, to avoid all temperature spikes, all eggs were placed in the incubators with the temperature controller set at 36° C., which prevents temperature spiking above 38° C. Once all the eggs were placed in the incubator and the lid firmly secured, the temperature controller was then raised to 38° C. It took the incubator approximately 60 minutes to equilibrate after placing the eggs in it in this fashion. Therefore incubation was reckoned to begin after this 60 minute period. All references herein to incubation periods are to be construed accordingly.

Eggs and methods of determining the sex of embryos

The chicken eggs were from Rhode Island Red hens and were purchased from a commercial supplier.

In preliminary investigations, embryos were recovered on days 3–12 inclusive, their abdomens opened and the animals sexed according to the relative size of the gonads. The gonads were also removed for histological sectioning to confirm their sex. The earliest time point for reliable sexing of the embryos was day 7 of incubation. All embryonic sexing reported In this study was performed on embryonic days 9,10,12,17, and 20. The embryonic day chosen did not affect the results.

Controls

In all experiments a control batch of eggs was incubated at a constant 38° C. throughout. This should produce a roughly 50/50 sex ratio, although in the Isabrown species, there is consistently a higher percentage of females, compared to males (sex ratio approximately 1: 0.9). If these control eggs showed significant mortality, i.e. above 10%, all experimental results were disregarded, and none of these are reported. This has happened on several occasions, and may be due to stress in the breeding stock, change in diet or other unrelated factors.

Collection of eggs from the hatchery

Eggs were collected from the birds shortly after laying. They were stored at the hatchery and transported at ambient temperature to Manchester University, where they were kept at ambient temperature for a maximum of 24 hours before commencing incubation. There is normally no development during this period. This is the normal poultry industry regime. If eggs are incubated immediately after laying, many embryos die.

Temperature shifting (pulsing)

At various times during incubation (as described in the Tables which follow) eggs were pulsed with either a higher or lower temperature for a variable pulse duration (as described in the Tables). Thus, for a shift on embryonic day 3, eggs were incubated for 72 hours (plus or minus 30 minutes) before the incubator was adjusted to pulse them, for example, at 22° C. for 48 hours (in the case of the two day pulse). Pulsing of the eggs was achieved by quickly placing the incubators in a cold room (4° C.) with the incubator lid ajar about 4 cm. This allowed for rapid cooling of the eggs within the incubator, which then rapidly equilibrated to its newly set temperature. Thus, for example, the incubator reached 22° C. within 15 minutes under this regime. The time at which the pulse temperature was reached was taken as the 0 time point for measuring the length of the pulse. In each experiment, 1 or 2 eggs were removed from the incubator at the commencement of the pulse time, opened and the embryo stage according to Hamburger and Hamilton criteria determined. Each incubator was carefully adjusted and monitored during the pulse period to maintain constant temperatures throughout the pulse.

Restoration of normal incubation condition

At the end of the pulse period, the incubator was then adjusted to bring the temperature back up to 38° C. This took no more than 30 minutes between setting the incubator controls and the eggs reaching their new temperature. Equally, there was no spiking of the incubator in terms of temperatures exceeding 38° C. The incubation of the eggs was continued at 38° C. until the time of termination (normally embryonic day 10 or day 17). During this time period, the incubator temperatures were constantly monitored with the platinum resistance thermometer probes, calibrated against the National Standard thermometer.

Examination of embryos (sexing and determining mortality)

At the end or the incubation period, the eggs were killed and opened and the embryos removed and staged according to the Hamburger-Hamilton method. All infertile eggs were noted and discarded from any further calculations. Eggs containing dead embryos were noted, and if possible, the sex of the embryo was determined (this is usually not possible). Of the remaining living embryos, these were opened and the embryo sexed by the macroscopic appearance of the gonads. In cases of doubt and in any case in one in five embryos, the gonads were removed and processed for histological sectioning. Sex was then diagnosed on the basis of gonadal differentiation into either testis or ovaries. The percentages of male, female and dead embryos in the Tables were derived in this way.

Genotyping

The heads of each of the embryos were removed and frozen at −70° C. This tissue was used to extract genomic DNA for slot blot hybridisation with a chicken W chromosome probe (Tone et al., 1982, Kodama et al., 1987, Saitoh et al., 1992, Saitoh and Mizuno 1992). This probe is a specific marker for the W chromosome and was used to confirm the genetic sex of the embryos. Slot blot analysis was only performed In experiments where there was a significant deviation of the sex ratio observed upon macroscopic and histological examination of the gonads. It served to confirm that the macroscopic phenotypic sex of the embryo differed from its genotypic sex on the basis of the W-chromosome probe.

Based on the macroscopic, histological and DNA analysis of sex determination, there was no difference in the accuracy of sexing embryos at any of the embryonic days/stages used. Moreover, in repeat experiments of the same temperature pulse conditions, there was no significant difference in the percentage of shift of the sex ratio dependent upon the embryonic age of sex determination. Confidence can therefore be placed in the accuracy and reproducibility of these sexing methods.

RESULTS

The data in Tables 1–3 clearly show that sex reversal occurs reliably and reproducibly under a certain set of conditions. Under other sets of conditions, sex reversal is not predictable, i.e. it happens some times, but not others, and under a wide range of conditions, there are no effects. This allows one to define a matrix of optimum conditions for alterations in the sex ratio. This can most easily be described by: timing of onset of the pulse, duration of the pulse, and temperature at which the eggs are pulsed.

Time of onset of the pulse in days and Hamburger Hamilton stages

The sensitive time window of development where a shift in temperature significantly affects the sex ratio, is between embryonic days 2–4 with the optimum on embryonic day 3. The term "on embryonic day n", n being a specified integer, as used herein, signifies that the pulsing took place when the eggs had been incubated for 24 n hours, plus or minus 30 minutes. Shifting the incubation temperature on or after embryonic day 5 has no effect on the sex ratio, but adversely effects the embryonic mortality. Experimental analysis was therefore concentrated on embryonic day 3.

An interesting early observation was that the stage of the embryo at the commencement of the pulse was very important. This meant that eggs which had been stored for too long before incubation began, gave variable results. This is illustrated clearly in Table 2, where a number of pulses on embryonic day 3 for similar periods of time and pulsing to similar temperatures gave unpredictable results. The reason is that the eggs used in the experiments in Table 2, varied in the length of storage between the time of egg laying and the commencement of incubation. This means that embryos were at different stages of development when commencing the time of the pulse. It was determined that it is important for optimal results to commence temperature pulsing at Hamburger-Hamilton stage 18/19, which is normally on embryonic day 3. The effects of pulsing on these days/stages are reproducible and are illustrated in Table 3. In practice, this means that eggs are kept for approximately 1 day (24–36 hours) between laying and the commencement of incubation. If eggs are stored for longer periods of time, it is important to titre the commencement of the temperature pulse, so that it begins at Hamburger-Hamilton stage 18/19.

Pulsing temperature to which the eggs are shifted

Optimum skews in the sex ratio towards an increase in males were observed when eggs were shifted on embryonic day 3 from their normal incubation temperature of about 38° C. to a temperature of about 22° C. (Tables 1 and 3). This produced at best a sex ratio of approximately 1.6 males for every female with a very low mortality figure (usually in the region of 5% which is the control level). Also, a shift to about 36° C. on embryonic day 3 reliably biased the sex ratio towards females, again with low mortality.

Shifting to other temperatures either has an unreliable effect on the sex ratio or causes substantial mortality of the eggs (Table 1).

Duration of the temperature pulse

Skews in the sex ratio were obtained with temperature pulses of 22° C. commencing on embryonic day 3 for variable periods between 8 and 48 hours. In general, long temperature pulses, i.e. exceeding 36 hours, usually produce increased mortality. Contrariwise, short temperature pulses have less reproducible effects. The optimum duration of the pulse seems to lie at around between 24 and 36 hours (Tables 1 and 3), but the results at shorter and longer pulse lengths indicate some latitude in these figures, say to a wider preferred range of 18 to 42 hours.

For temperature pulses at 36° C., preliminary experiments, reported in Table 1 of the priority application, carried out under less precisely defined conditions than given above, indicated that a pulse length of 2 to 4 days was particularly suitable and Table 1 below confirms. Again, there is some latitude in the lower figure, indicating a wider preferred range of 18 to 96 hours.

Age of the laying flock

To investigate the possible effects of flock age on the nature of the sex reversal obtained with temperature pulses during incubation, the optimum sex reversing regime i.e., a temperature pulse of 22° C. commencing on embryonic day 3, Hamburger-Hamilton stage 18/19 for varying periods of time, (Table 3), was used. Table 3 shows that the eggs of older parents show more of a sex skew than that of younger parents.

2. EFFECTS OF INCUBATION TEMPERATURE PULSING ON HATCHABILITY

To investigate whether the temperature pulsing regime adversely affected embryonic development and caused high late embryonic mortality or problems in hatching, the following experiment was established.

MATERIALS AND METHODS 400 eggs of the Isabrown auto-sexing strain were collected from the same flock of hens on Apr. 20, 1993. In the Isabrown strain, sex is closely related to feather colour, and hince, it is possible to sex the birds at hatching by looking at their feathers as an indicator of the genotypic sex. There is a less than 1% error claimed by the suppliers of these eggs in this feather sexing method. The Isabrown auto-sexing chickens are bred from pure parental lines. On hatching, the females are brown, later turning red, with white underfeathers. The males are yellow, later turning pure white. This auto-sexing characteristic is seen as early as embryonic day 12, when the feathers are being formed. In the embryo, the male feathers are transparent, whereas the female feathers are reddish brown. The percentage error in determining sex by feather in the embryo, compared to macroscopic inspection of the gonads, was determined to be less than 0.01%. The eggs were controlled in terms of parent of origin, age of the flock and age after egg laying. The eggs were placed in incubators on Apr. 21, 1993, as described previously. The pulsing regimes consisted of the following.

On embryonic day 3, i.e. at 72 hours (plus or minus 30 minutes) from the beginning of incubation, 100 eggs were pulsed at 22° C. for 24 hours and 300 eggs were pulsed at 36° C. for 48 hours.

On May 7, 1993, all eggs were removed from the incubators at the University of Manchester and candled. Candling allowed one to distinguish between fertile developing eggs, dead eggs or infertile eggs. At this stage, the dead or infertile eggs were removed and discarded. In the 36° C. group, 56 of the 300 eggs were infertile and none were dead, meaning that for the rest of the experiment, there was an effective starting group of 244 eggs. In the 22° C. shift group, 18 eggs were infertile and none were dead, i.e., the experiment started effectively with 82 eggs. Following the discard of these infertile eggs, the viable eggs were transported immediately to hatching incubators at the University of Liverpool Veterinary School, a distance of about 25 miles (45 km.). They were placed in these hatching incubators, so as to distinguish between the two treatment groups, i.e., 36° C. and 22° C. treatments, but all these hatching incubators were set at 38° C. Separation of the eggs in the treatment groups allowed for subsequent analysis on hatching.

The eggs hatched on May 13, 1993. The phenotypic sex of chickens on the day of hatching was determined by examining the macroscopic appearance of the vent of the bird. This is a common procedure in poultry practice, and is the basis for discarding male or female chickens under current poultry practice conditions. An experienced poultry vent sexer vent-sexed all the birds from these experiments on the day of hatching. He knew neither about the auto-sexing characteristics of the feathers of the Isabrown strain of birds, nor the details of the experimental treatment, i.e.

sexing at hatching was done "blind". All birds were then individually banded, so that they could be subsequently identified and traced to one of the experimental groups.

Results

Mortality

In the 36° C. treatment group, (starting with 244 eggs), 37 eggs did not hatch or died at the time of hatching. Of these, most of the birds died trying to get out of the shell. In order to emulate practice in the poultry industry, no attempt was made to assist the birds out of the shell. One chick died on the first day after hatching and four chicks died within the first two weeks of hatching, due to disease. So, in the 36° C. group, out of the total of 244 viable eggs, 85% hatched and 15% did not hatch.

In the 22° C. treatment group, of the 82 viable eggs in the experiment, 13 birds did not hatch, i.e. died on or before the time of hatching. Like the 36° C. group, the vast majority of these died on the day of hatching from a failure to get out of the shell. No chicks died in the first week. This means that out of a total of 82 viable eggs in the 22° C. pulse group, 84% hatched and 16% did not hatch.

The mortality figures in both groups are almost identical. This suggests that the mortality may have more to do with the conditions of the experiment, i.e. transporting the eggs to different incubators shortly after embryonic day 16, than to the pulsing regime. In any case, the maximum mortality as assayed at the time of hatching is likely to be around 15%.

Effects on sex at the time of hatching

The data are presented in Table 4 which documents genotypic sex, i.e. feather colour and phenotypic sex, i.e. vent sex in the various treatment groups. (The vent sexing is analogous to examination of the gonads of embryos).

In the 36° C. treatment group, in the 105 birds whose genotypic sex was male, there was complete concordance with the phenotypic sex. In the 101 birds whose genotypic sex was female, one bird was phenotypically male. This bird had a feather pattern which was intermediate between that of male and female. This is unlikely to be due to a temperature pulsing effect. The conclusion therefore is that 36° C. treatment had no effect in terms of sex reversal as assayed on the day of hatching. It can be regarded as a control experimental group for the purposes of sex reversal determination.

In the 22° C. group, of the 30 birds whose genotypic sex (feather colour) was male, there was again complete concordance between genotype and phenotype. However, of the 39 birds whose genotypic sex by feather colour was female, only 35 had the phenotypic sex of female, as determined by vent sexing. The other four had the phenotypic sex of male and were, therefore, "sex reversed", i.e. their genotype was female, but their phenotype male.

The sex reversed birds were reared under conventional poultry raising conditions for five months and they appeared to grow satisfactorily and maintain their phenotypic sex. Unfortunately, the birds were then killed by the sponsor who had agreed to pay for feeding them and this action occurred without any warning to the inventor or patent applicant. Nevertheless, the experiment clearly demonstrated that the temperature pulsing regime does not produce a significant mortality in terms of hatching, that adult birds whose phenotypic sex differs from their genotypic sex were produced and that these birds can develop and grow normally.

Implications

The unexpected finding that manipulation of incubation temperature in domestic chickens can influence the sex ratio, without the high mortalities reported by Shubina et al., may be important in a number of ways. First, it will be possible to skew the sex ratio towards either females for egg laying species or males for species required for maximal growth. Second, it is possible to generate by this invention, birds whose phenotypic sex is different from their genotypic sex, e.g. ZW males. When such birds breed, the new stock would produce a skewed sex ratio in subsequent generations, even if all the eggs were incubated at 38° C. This may be very important for commercial businesses which supply stock into the poultry industry. Thus, the invention includes a method of producing birds of an avian species which are chromosomally male (ZZ) but phenotypically female or chromosomally female (ZW) but phenotypically male, which comprises hatching eggs by a method of the invention, above defined, to bias the phenotypic sex ratio, detecting the chromosome type of the hatchlings and selecting hatchlings which are chromosomally male but phenotypically female or vice versa. It further includes rearing the hatchlings to an adult age at which they are capable of breeding. Still further, it includes allowing the phenotypically female or male birds (chromosomally ZZ or ZW respectively), to breed with a bird of the opposite phenotypic sex of normal chromosome type (chromosally ZZ or ZW respectively), to produce offspring which are chromosomally homogenetic individuals (all WW).

Third, it ought to be possible to do the same things in other commercially important avian species. These include, for example, turkeys or pheasant for commercial purposes i.e. human food. They also include valuable species of birds in the pet trade e.g. parrots, rare or endangered species where one wishes to influence the sex ratio for breeding purposes. In principle, the mechanism should be applicable to all avian species.

Translating the requirements of the method of the invention to other avian species, the temperature shift should be timed to take place at a time of between 2 and 4 days, preferably about 3–3.5 days, before the first time at which sexual differentiation can be detected histologically, and for a period of time which enables the pulse to be completed before the time at which sexual differentiation occurs in control birds and is not less than 18 hours.

Other ways of creating shifted conditions

The inventor believes that the reason for the improvement in the mortality rates following shifts of the incubation temperature relates to gas and humidity exchange across the egg shell. When one moves from the baseline incubation temperature to the shifted temperature and then back to or near the baseline temperature, there are occasions when the egg is warmer than the incubator, in which case, the egg will lose gas and humidity from the eggshell membrane. Conversely, there are times when the incubator is warmer than the egg, in which case, it will take up gases and water vapour. This may be important in improving the respiratory exchange of the developing embryo. In nature, where incubation mortalities are lower, the temperature of egg incubation is likely to oscillate much more than in an artificial incubator. Those skilled in the art will therefore be able to find other means of altering the ambient environment by use of changes in vapour pressure.

DATA FOR TEMPERATURE PULSE EXPERIMENTS

DP=Day of Incubation after which pulse was applied (24 hour days)

PL=Pulse Length (Hours) PT-Pulse temperature (C)
M=Males F=females D=Dead

TABLE 1

| DP | PL (Hrs) | PT (°C.) | # M | % M | # F | % F | # D | % D |
|---|---|---|---|---|---|---|---|---|
| 1 | 24 | 35 | 5 | 50.0 | 5 | 50.0 | 0 | 0 |
| 2 | 24 | 18 | 18 | 36.0 | 27 | 54.0 | 5 | 10.0 |
| 2 | 24 | 18 | 17 | 34.7 | 26 | 53.1 | 6 | 12.2 |
| 2 | 48 | 18 | 22 | 44.9 | 18 | 36.7 | 9 | 18.4 |
| 2 | 48 | 18 | 26 | 50.o | 19 | 36.5 | 7 | 13.5 |
| 2 | 24 | 20 | 23 | 44.2 | 28 | 53.9 | 1 | 1.9 |
| 3 | 48 | 20 | 27 | 50.9 | 19 | 35.9 | 7 | 73.2 |
| 3 | 8 | 22 | 26 | 56.5 | 17 | 37.0 | 3 | 6.5 |
| 3 | 8 | 22 | 27 | 50.0 | 23 | 42.6 | 4 | 7.4 |
| 3 | 8 | 22 | 29 | 50.9 | 26 | 45.6 | 2 | 3.5 |
| 3 | 24 | 22 | 25 | 54.3 | 19 | 41.3 | 2 | 4.4 |
| 3 | 24 | 22 | 24 | 52.2 | 19 | 41.3 | 3 | 6.5 |
| 3 | 24 | 22 | 27 | 47.3 | 29 | 50.9 | 1 | 1.8 |
| 3 | 24 | 22 | 35 | 54.7 | 25 | 39.1 | 4 | 6.2 |
| 3 | 24 | 22 | 27 | 48.2 | 23 | 41.1 | 6 | 10.7 |
| 3 | 36 | 22 | 35 | 61.4 | 21 | 36.8 | 1 | 1.8 |
| 3 | 36 | 22 | 26 | 50.0 | 25 | 48.1 | 1 | 1.9 |
| 3 | 36 | 22 | 32 | 51.6 | 25 | 40.3 | 5 | 8.1 |
| 3 | 36 | 22 | 34 | 55.7 | 22 | 36.1 | 5 | 8.2 |
| 3 | 36 | 22 | 33 | 60.0 | 20 | 36.4 | 2 | 3.6 |
| 3 | 48 | 22 | 24 | 54.5 | 13 | 29.5 | 7 | 16.0 |
| 3 | 48 | 22 | 30 | 53.6 | 21 | 37.5 | 5 | 8.9 |
| 3 | 48 | 22 | 20 | 40.8 | 21 | 42.9 | 8 | 16.3 |
| 3 | 48 | 36 | 6 | 28.6 | 14 | 66.6 | 1 | 4.8 |
| 3 | 72 | 36 | 8 | 38.1 | 12 | 57.1 | 1 | 4.8 |
| 3 | 96 | 36 | 14 | 43.8 | 17 | 53.1 | 1 | 3.1 |
| 4 | 48 | 33 | 9 | 40.9 | 11 | 50.0 | 2 | 9.1 |
| 4 | 72 | 33 | 2 | 11.1 | 5 | 27.8 | 11 | 61.1 |
| 4 | 72 | 33 | 2 | 15.4 | 5 | 38.5 | 6 | 46.1 |
| 4 | 96 | 33 | 3 | 13.6 | 1 | 4.6 | 18 | 81.8 |
| 4 | 48 | 34 | 8 | 33.3 | 13 | 54.2 | 3 | 12.5 |
| 4 | 72 | 34 | 6 | 27.3 | 10 | 45.4 | 6 | 27.3 |
| 4 | 96 | 34 | 5 | 20.8 | 4 | 16.7 | 15 | 62.5 |
| 4 | 48 | 35 | 10 | 45.5 | 9 | 40.9 | 3 | 13.6 |
| 4 | 48 | 35 | 11 | 50.0 | 11 | 50.0 | 0 | 0 |
| 4 | 72 | 35 | 28 | 50.0 | 23 | 41.1 | 5 | 8.9 |
| 4 | 72 | 35 | 6 | 40.0 | 9 | 60.0 | 0 | 0 |
| 4 | 96 | 35 | 8 | 42.1 | 7 | 36.8 | 4 | 21.1 |
| 4 | 48 | 36 | 7 | 33.3 | 6 | 28.6 | 8 | 38.1 |
| 4 | 72 | 36 | 7 | 30.4 | 13 | 56.5 | 3 | 13.1 |
| 4 | 96 | 36 | 5 | 22.7 | 17 | 77.3 | 0 | 0 |
| 4 | 96 | 36 | 25 | 47.2 | 26 | 49.0 | 2 | 3.8 |
| 4 | 48 | 37 | 13 | 54.2 | 11 | 45.8 | 0 | 0 |
| 4 | 72 | 37 | 4 | 19.0 | 16 | 76.2 | 1 | 4.8 |
| 4 | 96 | 37 | 9 | 33.3 | 11 | 40.7 | 7 | 26.0 |
| 5 | 48 | 33 | 10 | 45.5 | 11 | 50.0 | 1 | 4.5 |
| 5 | 72 | 33 | 4 | 19.1 | 2 | 9.5 | 15 | 71.4 |
| 5 | 96 | 33 | 2 | 9.1 | 1 | 4.5 | 19 | 86.4 |
| 5 | 48 | 34 | 10 | 45.5 | 7 | 31.8 | 5 | 22.7 |
| 5 | 72 | 34 | 8 | 32.0 | 16 | 64.0 | 1 | 4.0 |
| 5 | 96 | 34 | 17 | 63.0 | 8 | 29.6 | 2 | 7.4 |
| 5 | 96 | 34 | 23 | 43.4 | 22 | 41.5 | 8 | 15.1 |
| 5 | 48 | 35 | 9 | 39.1 | 72 | 52.2 | 2 | 8.7 |
| 5 | 72 | 35 | 10 | 45.5 | 9 | 40.9 | 3 | 13.6 |
| 5 | 96 | 35 | 14 | 43.8 | 13 | 40.6 | 5 | 15.6 |
| 5 | 48 | 36 | 10 | 26.3 | 13 | 34.2 | 15 | 39.5 |
| 5 | 72 | 36 | 14 | 48.3 | 10 | 34.5 | 5 | 17.2 |
| 5 | 96 | 36 | 10 | 40.0 | 7 | 28.0 | 8 | 32.0 |
| 5 | 48 | 37 | 4 | 17.4 | 2 | 8.7 | 77 | 73.9 |
| 5 | 72 | 37 | 3 | 13.0 | 3 | 13.0 | 17 | 74.0 |
| 5 | 96 | 37 | 4 | 77.4 | 5 | 27.7 | 14 | 60.9 |
| 6 | 48 | 34 | 13 | 31.0 | 19 | 45.2 | 10 | 23.8 |
| 6 | 72 | 34 | 13 | 43.3 | 13 | 43.3 | 4 | 13.4 |
| 6 | 48 | 35 | 9 | 45.0 | 10 | 50.0 | I | 5.0 |
| 6 | 72 | 35 | 2 | 33.3 | 30 | 50.0 | 10 | 16.7 |
| 6 | 96 | 35 | 77 | 52.4 | 6 | 28.6 | 4 | 19.0 |
| 6 | 48 | 37 | 1 | 4.0 | 2 | 8.0 | 22 | 88.0 |
| 6 | 72 | 37 | 2 | 8.3 | 1 | 4.2 | 21 | 87.5 |
| CONTROL | | 38 | 18 | 45.0 | 20 | 50.0 | 2 | 5.0 |
| CONTROL | | 38 | 20 | 52.6 | 17 | 44.7 | 1 | 2.6 |
| CONTROL | | 38 | 11 | 45.8 | 13 | 54.2 | 0 | 0 |
| CONTROL | | 38 | 25 | 44.6 | 27 | 48.2 | 4 | 7.2 |
| CONTROL | | 38 | 18 | 40.9 | 20 | 45.5 | 6 | 13.6 |
| CONTROL | | 38 | 25 | 47.2 | 28 | 52.8 | 0 | 0 |

TABLE 1-continued

| DP | PL (Hrs) | PT (°C.) | # M | % M | # F | % F | # D | % D |
|---|---|---|---|---|---|---|---|---|
| CONTROL | | 38 | 21 | 42.9 | 25 | 51.0 | 3 | 6.1 |
| CONTROL | | 38 | 23 | W.4 | 32 | 56.1 | 2 | 3.5 |
| CONTROL | | 38 | 26 | 44.1 | 30 | 50.8 | 3 | 5.1 |

DATA FOR TEMPERATURE PULSE EXPERIMENTS

DP=Day of Incubation after which pulse was applied (24 hour days)
PL=Pulse Length (Hours) PT=Pulse temperature (C)
M=Males F=females D=Dead

TABLE 2

| DP | PL (Hrs) | PT (°C.) | # M | % M | # F | % F | # D | % D |
|---|---|---|---|---|---|---|---|---|
| 3 | 48 | 20 | 27 | 50.9 | 19 | 35.9 | 7 | 13.2 |
| 3 | 8 | 22 | 26 | 56.5 | 17 | 37.0 | 3 | 6.5 |
| 3 | 24 | 22 | 25 | 54.3 | 19 | 41.3 | 2 | 4.4 |
| 3 | 24 | 22 | 24 | 52.2 | 19 | 41.3 | 3 | 6.5 |
| 3 | 48 | 22 | 20 | 40.0 | 16 | 32.0 | 14 | 28.0 |
| 3 | 48 | 22 | 27 | 50.9 | 18 | 34.0 | 8 | 15.1 |
| 3 | 48 | 22 | 17 | 29.8 | 30 | 52.6 | 10 | 17.6 |
| 3 | 48 | 22 | 19 | 35.9 | 28 | 52.8 | 6 | 11.3 |
| 3 | 48 | 22 | 13 | 37.1 | 18 | 51.5 | 4 | 11.4 |
| 3 | 48 | 22 | 18 | 45.0 | 17 | 42.5 | 5 | 12.5 |
| 3 | 48 | 22 | 15 | 45.5 | 15 | 45.5 | 3 | 9.0 |
| 3 | 48 | 22 | 31 | 43.1 | 33 | 45.8 | 8 | 11.7 |
| 3 | 48 | 22 | 35 | 47.9 | 32 | 43.9 | 6 | 8.2 |
| 3 | 48 | 22 | 24 | 54.5 | 13 | 29.5 | 7 | 16.0 |
| 3 | 48 | 22 | 15 | 36.6 | 15 | 36.6 | 11 | 26.8 |
| 3 | 48 | 25 | 3 | 14.3 | 4 | 19.0 | 14 | 66.7 |
| 3 | 24 | 26 | 9 | 34.6 | 13 | 50.0 | 4 | 15.4 |
| 3 | 48 | 33 | 7 | 31.8 | 11 | 50.0 | 4 | 18.2 |
| 3 | 72 | 33 | 5 | 21.7 | 12 | 52.2 | 6 | 26.1 |
| 3 | 96 | 33 | 7 | 33.3 | 1 | 4.8 | 13 | 61.9 |
| 3 | 48 | 36 | 6 | 28.6 | 14 | 66.6 | 1 | 4.8 |
| 3 | 72 | 36 | 8 | 38.1 | 12 | 57.7 | 1 | 4.8 |
| 3 | 96 | 36 | 14 | 43.8 | 17 | 53.1 | 1 | 3.1 |

DATA FOR TEMPERATURE PULSE EXPERIMENTS

PT = Pulse temperature (C.)  M = Males
PL = Pulse Length (Hours)  F = females
AF = Age of laying flock (Weeks)  D = Dead
EA = Age of egg from time of lay (Hours)
Temperature Pulse was applied at day 3 of incubation.
Number of eggs used in each experiment = 63

TABLE 3

| PT (°C.) | PL (Hrs) | EA (Hrs) | AF (Wks) | % M | % F | % D | M:F |
|---|---|---|---|---|---|---|---|
| 22 | 8 | 18 | 52 | 56.5 | 37.0 | 6.5 | 1.53:1 |
| 22 | 8 | 36 | 34 | 50.0 | 42.6 | 7.4 | 1.17:1 |
| 22 | 8 | 30 | 37 | 46.0 | 50.0 | 4.0 | 0.92:1 |
| 22 | 8 | 36 | 35 | 50.9 | 45.6 | 3.5 | 1.12:1 |
| 22 | 24 | 18 | 52 | 52.2 | 41.3 | 6.5 | 1.26:1 |
| 22 | 24 | 36 | 30 | 47.3 | 50.9 | 1.8 | 0.93:1 |
| 22 | 24 | 36 | 34 | 54.7 | 39.1 | 6.2 | 1.40:1 |
| 22 | 24 | 36 | 37 | 48.2 | 41.1 | 70.7 | 1.17:1 |
| 22 | 36 | 36 | 32 | 61.4 | 36.8 | 1.8 | 1.67:1 |
| 22 | 36 | 36 | 32 | 50.0 | 48.7 | 1.9 | 1.04:1 |
| 22 | 36 | 36 | 33 | 55.7 | 36.1 | 8.2 | 1.54:1 |
| 22 | 36 | 30 | 37 | 59.2 | 40.8 | 0 | 1.45:1 |

TABLE 3-continued

| PT (°C.) | PL (Hrs) | EA (Hrs) | AF (Wks) | % M | % F | % D | M:F |
|---|---|---|---|---|---|---|---|
| 22 | 36 | 36 | 33 | 51.6 | 40.3 | 8.1 | 7.28:1 |
| 22 | 48 | 18 | 52 | 54.5 | 29.5 | 16.0 | 1.85:1 |
| 22 | 48 | 30 | 36 | 54.0 | 38.1 | 7.9 | 1.42:1 |
| 22 | 48 | 36 | 30 | 53.6 | 37.5 | 8.9 | 1.43:1 |
| 22 | 48 | 36 | 30 | 40.8 | 42.9 | 16.3 | 0.95:1 |
| CONTROL | | 36 | 34 | 40.4 | 56.1 | 3.5 | 0.72:1 |
| CONTROL | | 30 | 37 | 43.8 | 46.9 | 9.3 | 0.93:1 |
| CONTROL | | 30 | 37 | 43.8 | 53.1 | 3.1 | 0.82:1 |
| CONTROL | | 36 | 32 | 44.1 | 50.8 | 5.1 | 0.87:1 |

TABLE 4

GENOTYPIC AND PHENOTYPIC SEXING OF THE CHICKS ON THE DAY OF HATCHING

| TREATMENT GROUP | GENOTYPIC SEX (FEATHER COLOUR) | PHENOTYPIC SEX (VENT SEX) |
|---|---|---|
| 22° C. | 30 male | 30 male, 0 female |
| 22° C. | 39 female | 35 female, 4 male |
| 36° C. | 105 male | 105 male, 0 female |
| 26° C. | 101 female | 100 female, 1 male |

References

Bennett A. F. and Dawson N. R. (1979). Physiological responses of embryonic Heermann's gulls to temperature. Physiol. Zool. 52: 413–421.

Deeming D. C. and Ferguson W. R. (1988). Environmental regulation of sex determination in reptiles. Phil. Trans. Roy. Soc. London (B) 322: 19–39.

Shubina G. N., Zhmurin L. M. and Vendeneeva V. A. (1972). Effect of short-term temperature drop of egg incubation on sex determination of chicken embryos. TR. Vses. Nauch-Issled. Inst. Fizziol. Biokhim. Pitan. Selskokhoz Zhivotn. 11: 260–268.

Sittman K. (1984) Sex determination in birds: Progeny of nondisjunction canaries of Durham (1926), Genetic Research, Cambridge 43: 173–180.

Tone M. et al (1982) Demonstration of W chromosome-specific repetitive DNA sequences In the domestic fowl Galus Galus domesticus. Chromosoma, 86: 551–569: see also Kodama et al (1987) Chromosoma 96: 18–25; Saitoh et al (1991) Chromosoma 101: 32–40; and Saitoh & Mizuno (1992) Chromosoma 101: 474–477.

Tazawa H. and Rahn H. (1986). Tolerance of chick embryos to low temperatures in reference to the heart rate. Comp. Biochem. Physiol. 85A: 531–534.

I claim:

1. A method of hatching eggs of avian species which comprises carrying out at least one cycle of steps (a) to (c) as follows:
   (a) incubating the eggs in a first, baseline ambient environment which is normal for hatchery incubation of the eggs of the avian species In the prevailing climatic conditions and then during a sex-sensitive time window of embryonic development, (b) altering the ambient environment to shifted conditions for a period of time effective to bias the normal phenotypic sex ratio of the embryos, without significant adverse effect on the average mortality rate, and (c) thereafter restoring the incubation conditions to or towards normal, and allowing the eggs to hatch.

2. A method according to claim 1, wherein the avian species is a chicken.

3. A method according to claim 2 wherein the shifted conditions comprise reduced temperature.

4. A method according to claim 3 wherein the temperature is reduced when the eggs are at Hamilton-Hamburger stage 18 or 19 or at 2–4 days after an incubation which began from 18 to 36 hours after the eggs were laid.

5. A method according to claim 4, wherein the shifted temperature is maintained at about 22° C. for a period of from 18 to 42 hours.

6. A method according to claim 5 wherein the period of shifted temperature is from 24 to 36 hours.

7. A method according to claim 4, wherein the shifted temperature is maintained at about 36° C. for a period of from 18 to 96 hours.

8. A method according to claim 7 wherein the period of shifted temperature is from 24 to 72 hours.

9. A method of producing birds of an avian species which are chromosomally male (ZZ) but phenotypically female or chromosomally female (ZW) but phenotypically male, which comprises hatching eggs to bias the phenotypic sex ratio, by carrying out at least one cycle of steps (a) to (c) as follows: (a) incubating the eggs in a first, baseline ambient environment which is normal for hatchery incubation of the eggs of the avian species in a prevailing climatic conditions and then during a sex-sensitive time window of embryonic development, (b) altering the ambient environment to bias the normal phenotypic sex ratio of the embryos, without significant adverse effect on the average mortality rate, and (c) thereafter restoring the incubation conditions to or towards normal, and allowing the eggs to hatch, detecting the chromosome type of the hatchlings and selecting hatchlings which are chromosomally male but phenotypically female or vice versa.

10. A method according to claim 9 which further comprises rearing the hatchlings to an adult age at which they are capable of breeding.

11. A method according to claim 10 which further comprises allowing the phenotypically female or male birds (chromosomally ZZ or ZH respectively), to breed with a bird of the opposite phenotypic sex of normal chromosome type (chromosomally ZZ or ZW respectively), to produce offspring which are chromosomally homogenetic individuals (all WW).

12. An incubator for hatching avian eggs adapted to provide at least one of the following cycle of conditions: (a) incubating the eggs in a first, baseline ambient environment which is normal for hatchery incubation of the eggs of the avian species in the prevailing climatic conditions and then during a sex-sensitive time window of embryonic development, (b) altering the ambient environment to shifted conditions for a period of time effective to bias the normal phenotypic sex ratio of the embryos, without significant adverse effect on the average mortality rate, and (c) thereafter restoring the incubation conditions to or towards normal, and allowing the eggs to hatch.

13. An incubator according to claim 12 adapted by the provision of associated programmable control means for varying the conditions.

* * * * *